United States Patent [19]

Kvitko et al.

[11] Patent Number: 5,610,305
[45] Date of Patent: Mar. 11, 1997

[54] PYRAZOLE-AND PIPERIDINE-CONTAINING COMPOUNDS AND THEIR METAL COMPLEXES AS LIGHT STABILIZERS

[75] Inventors: Idel Y. Kvitko, Ashdod; Jack Azran, Ashkelon, both of Israel

[73] Assignee: UV Stab Ltd., Ashkelon, Israel

[21] Appl. No.: 561,655

[22] Filed: Nov. 22, 1995

[51] Int. Cl.$^6$ .......................... C07D 401/00; C07F 1/08; C07F 3/06
[52] U.S. Cl. ................................ 546/6; 546/11; 546/211
[58] Field of Search ................................ 546/211, 6, 11

[56] References Cited

U.S. PATENT DOCUMENTS

| | | | |
|---|---|---|---|
| 3,975,382 | 8/1976 | Avar et al. | 260/240 G |
| 4,146,540 | 3/1979 | Avar et al. | 260/299 |
| 4,194,989 | 3/1980 | Irick, Jr. et al. | 252/400 A |
| 4,231,921 | 11/1980 | Moser | 260/46.75 R |
| 4,247,694 | 1/1981 | Rasberger | 546/11 |

FOREIGN PATENT DOCUMENTS

| | | |
|---|---|---|
| 891814 | 7/1982 | Belgium . |
| 2410370 | 9/1974 | Germany . |
| 2433111 | 1/1975 | Germany . |
| 2511354 | 9/1975 | Germany . |
| 2519594 | 11/1975 | Germany . |
| 2529052 | 1/1976 | Germany . |
| 2651272 | 8/1977 | Germany . |
| 605796 | 10/1978 | Switzerland . |
| 717043 | 2/1980 | U.S.S.R. . |
| 737401 | 6/1980 | U.S.S.R. . |
| 786314 | 11/1980 | U.S.S.R. . |
| 956504 | 9/1982 | U.S.S.R. . |
| 1005448 | 12/1982 | U.S.S.R. . |
| 1205543 | 11/1985 | U.S.S.R. . |

OTHER PUBLICATIONS

"Atmospheric Oxidation and Antioxidants", G. Scott, Editor, Elsevier, 1993, vol. I, Chap. 2 (Al–Malaika –Autoxidation), vol. I, Chap 4 (Scott –Antioxidants: Chain Breaking Mechanisms), vol. I, Chap. 5 (Al–Malaika—Antioxidants—Preventive Mechanisms), vol. II Chap 3 (Scott—Oxidation and Stabilization of Polymers During Processing), vol. II, Chap. 4 (Billingham—The physical Chemistry of Polymer Oxidation and Stabilization), vol. II, Chap. 5 (Scott—Macromolecular and Polymer–Bound Antioxidants), vol. II, Chap. 6 (Osawa—Metal Catalysed Oxidation and its Inhibition), vol. II, Chap. 8 (Scott—Photodegradation and Photostabilization of Polymers), vol. II, Chap. 9, (Scott—Synergism and Antagonism).

Pospisil, J., "Current Status of Exploitation of Radical Scavenging Stabilizers in Advanced Polymer Stabilization", Die Angewandte Makromolekulare Chemie, 216 (1994) pp. 135–146.

Gugumus, F., "New Trends in the Stabilization of Polyolefin Fibers", Polymer–Degradation and Stability, 44 (1994) pp. 273–297.

Pospisil, J., "Functionalized Oligomers and Polymers as Stabilizers for Conventional Polymers" (1990).

B. A. Posai–Koshiz and I. Y. Kvitko, "The Interaction of Aminomethylene Derivatives of Azoles with Phosphorus Oxytrichloride", J. Org. Khim, vol. 1, pp. 169–173 (1966) in Russian with English Abstract.

I. Y. Kvitko, J. Org. Khim, vol. 5, pp. 1685–1692 (1969) in Russian.

B. A. Pozai–Koshiz and I. Y. Kvitko, "Interaction of Compounds Containing Active Hydrogen Atoms with Substituted Amides", J. Org. Khim, vol. 32, pp. 4050–4056 (1962) in Russian, English Abstract.

B. A. Pozai–Koshiz and I. Y. Kvitko, "The Chemical Transformation of N,N–disubstituted Aminomethylene Derivatives of 5–pyrazolinone and Rhodanine", J. Org. Khim, vol. 34, pp. 2999–3005 (1964) in Russian with English Abstract.

B. I. Stepanov, "Introduction to the Chemistry and Technology of Organic Dyes", Chemistry, Moscow, (1977) pp. 252–268 in Russian with English Abstract.

Freyer et al., Pyrazolone derivatives, J. Prakt. Chemie., Band 319, Heft 6, 1977, pp. 905–910 1977.

*Primary Examiner*—Mukund J. Shah
*Assistant Examiner*—Deepak R. Rao
*Attorney, Agent, or Firm*—Mark M. Friedman

[57] ABSTRACT

Novel pyrazole-containing compounds useful as light-stabilizers for polymers, their Ni, Zn, Cu, and Co metal complexes, and methods for the synthesis of such complexes are provided. The compounds include a hindered amine light stabilizer (HALS) such as a substituted piperidine, thereby incorporate the properties of UV absorbers and redical scavengers. The compounds are of the formulas I and II,

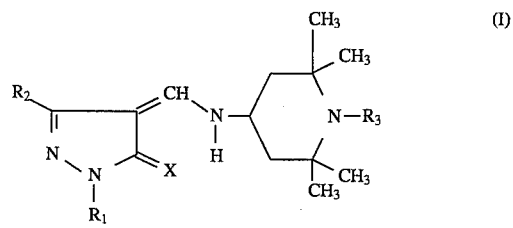

(I)

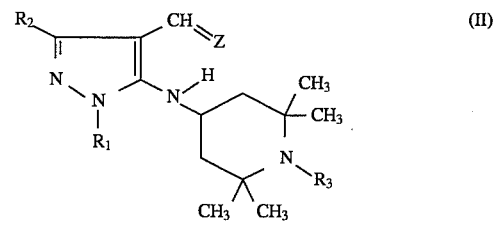

(II)

where $R_1$ is phenyl, $R_2$ is methyl, X is oxygen or sulphur, Z is oxygen or N-aryl, and $R_3$ is hydrogen, alkyl, a derivative of carboxyacryloyl or carboxybenzoyl or a derivative of pyrazole. The compounds and their metal complexes are highly compatible with various polymers, thermostable, and retain their photostability under conditions of continuous and intensive irradiation. Methods for the synthesis of metal complexes include the reaction of: (a) a compound with metal acetate; or (b) a metal complex with anhydride or a pyrazole derivative.

20 Claims, 6 Drawing Sheets

| | |
|---|---|
| I | R = H, X = 0; |
| II | R = H, X = S; |
| III | R = H, Z = 0; |
| IV | R = CH$_3$, X = 0; |
| V | R = COCH=CHCOOH, X = 0; |
| VI | R = CO-C(=CH$_2$)-CH$_2$COOH, X = 0; |
| VII | R = COC$_6$H$_4$COOH (o-), X = 0; |
| VIII | R = COC$_6$H$_4$COOH (o-), X = S; |
| IX | R = COC$_6$H$_4$COOH (o-), Z = 0; |
| X | R = 3-Me-1-Ph-5-pyrazolonylmethylidene-4, X = 0; |
| XI | R = 3-Me-1-Ph-5-thiopyrazolonylmethylidene-4, X = 0; |
| XII | R = 3-Me-1-Ph-5-pyrazolonylmethylidene-4, Z = 0; |
| XIII | R = 3-Me-1-Ph-5-thiopyrazolonylmethylidene-4, Z = 0; |
| XIV | R = 3-Me-1-Ph-5-pyrazolonylmethylidene-4, Z = NC$_6$H$_4$OC$_6$H$_5$; |
| XV | R = 3-Me-1-Ph-5-pyrazolonylmethylidene-4, X = S; |
| XVI | R = 3-Me-1-Ph-5-thiopyrazolonylmethylidene-4, X = S. |

XVII   R = H, X = 0, Me = Zn;

XVIII  R = H, X = 0, Me = Ni;

XIX    R = H, X = 0, Me = Cu;

XX     R = H, X = S, Me = Zn;

XXI    R = H, X = S, Me = Co;

XXII   R = H, X = S, Me = Cu;

XXIII  R = H, Z = 0, Me = Zn;

XXIV   R = CH$_3$,    X = 0, Me = Ni;

XXV    R = CH$_3$,    X = S, Me = Zn.

| | | |
|---|---|---|
| XXVI | R = COCH=CHCOOH, | X = O, Me = Zn; |
| XXVII | R = CO-C-CH$_2$COOH,<br>$\parallel$<br>CH$_2$ | X = O, Me = Zn; |
| XXVIII | R = COC$_6$H$_4$COOH (o-), | X = O, Me = Zn; |
| XXIX | R = COC$_6$H$_4$COOH (o-), | X = O, Me = Ni; |
| XXX | R = 3-Me-1-Ph-5-pyrazolonylmethylidene-4,<br>X = O, Me = Zn; | |
| XXXI | R = 3-Me-1-Ph-5-thiopyrazolonylmethylidene-4,<br>X = O, Me = Zn; | |
| XXXII | R = 3-Me-1-Ph-5-pyrazolonylmethylidene-4,<br>X = O, Me = Co; | |
| XXXIII | R = 3-Me-1-Ph-5-pyrazolonylmethylidene-4,<br>X = O, Me = Cu; | |
| XXXIV | R = 3-Me-1-Ph-5-thiopyrazolonylmethylidene-4,<br>X = S, Me = Zn; | |
| XXXV | R = 3-Me-1-Ph-5-thiopyrazolonylmethylidene-4,<br>X = S, Me = Ni; | |
| XXXVI | R = 3-Me-1-Ph-5-pyrazolonylmethylidene-4,<br>Z = NC$_6$H$_5$, Me = Cu; | |
| XXXVII | R = 3-Me-1-Ph-5-pyrazolonylmethylidene-4,<br>Z = NC$_6$H$_4$OC$_6$H$_5$, Me = Zn; | |
| XXXVIII | R = 3-Me-1-Ph-5-thiopyrazolonylmethylidene-4,<br>Z = NC$_6$H$_5$, Me = Zn; | |
| XXXIX | R = 3-Me-1-Ph-5-thiopyrazolonylmethylidene-4,<br>Z = NC$_6$H$_4$OC$_6$H$_5$, Me = Cu; | |
| XL | R = 3-Me-1-Ph-5-pyrazolonylmethylidene-4,<br>Z = NC$_6$H$_4$COOC$_4$H$_9$ (m-), Me = Cu; | |
| XLI | R = 3-Me-1-Ph-5-pyrazolonylmethylidene-4,<br>Z = NC$_6$H$_4$NHC$_6$H$_5$ (p-), Me = Cu; | |
| XLII | R = 3-Me-1-Ph-5-pyrazolonylmethylidene-4,<br>Z = NC$_6$H$_2$[p-OH,m,m'-C(CH$_3$)$_3$], M = Cu. | |

PYRAZOLE-AND PIPERIDINE-CONTAINING COMPOUNDS AND THEIR METAL COMPLEXES AS LIGHT STABILIZERS

FIELD AND BACKGROUND OF THE INVENTION

The present invention relates to novel pyrazole derivatives and their use as light stabilizers for inhibiting the degradation of various polymers and, more particularly, to compounds which incorporate UV absorbers such as pyrazole derivatives and radical scavengers such as hindered amine light stabilizers (HALS), metal complexes of such compounds, and methods for the synthesis of such metal complexes.

Various industrial applications require the use of polymers which are durable and resistant to ultraviolet light. Examples for such applications can be found in the fields of agriculture, building, manufacture of coatings, machine and aircraft constructions and space exploration.

However, many of the polymers used, such as polyester, polyethylene (LD and HD), polypropylene, polystyrene and polycarbonate are susceptible to photodegradation induced by ultraviolet (UV) light, present in sunlight and various kinds of light sources.

The chemical effects of UV irradiation on such polymers are rooted in the presence of carbonyl groups which may have been formed by various uncontrolled reactions during the synthesis or the processing of the polymer. When these carbonyl groups are exposed to UV-light, they are easily excited to singlet and triplet states which could subsequently initiate some of a number of photochemical reactions in which free radicals are a main product.

Thus, the oxidative degradation of polymers is due to a propagation reaction which involves the formation of free radicals such as alkyl (R.) and peroxy (ROO.) radicals, and compounds such as hydroperoxides (ROOH) which easily decompose to free radicals of the type R., RO., and ROO.. Such radicals may take part in further attacks of additional polymer molecules. These repeated radical attacks may result in scission and crosslinking of polymer chains, while scission may turn a solid polymer into a thin liquid and crosslinking may create a brittle polymer network.

Various attempts have been made to develop light stabilizers which inhibit the photodegradation of polymers. These light stabilizers can be classified according to their stabilization mechanisms into several groups, such as: (a) UV absorbers (UVAs), which absorb the harmful UV light and re-emit it as vibrational (thermal) energy without being themselves destroyed, and without sensitizing the oxydation of the polymer; (b) excited state quenchers, which deactivate the excited states (singlet or triplet) of the polymer, by a mechanism of energy transfer which occur between an excited chromophore in the polymer molecule (donor) and the photostabilizer molecule (acceptor); (c) hydroperoxide (ROOH) decomposers which decompose hydroperoxide molecules to non-radical products such as ions; and (d) radical scavengers, which react with free radicals such as R., RO. and ROO., to form non-radical products such as olefins and ions, or stable radicals such as nitroxyl.

Further attempts have been made to incorporate two or more components acting according to the above stabilization mechanisms, such as a UV absorber and an excited state quencher, a UV absorber and a hydroperoxide decomposer, and a UV absorber and a radical scavenger, since such compounds show a synergistic behavior, in which the UV absorber protects the other component from distruction by UV-light, and said other component inhibit the formation of free radicals and thereby extends the useful life of the UV-absorber (see, for example, J. Pospisil, P. P. Klemchuk, "Oxidation Inhibition in Organic Materials", Vol. 1&2, CRC Press, Bola Raton, 1990; G. Scott, "Atmospheric Oxidation and Antioxidants", Elsevier, A-L-NY-T, Vol 1,2,3, 1993; J. Pospisil, Angew. Macromol. Chem. 216 (1994), pp. 135–146; arid F. Gugumas, "Polym. Degrad. and Stab.", 44 (1994), pp.273–297 and references cited therein).

Considerable efforts have been made to develop pyrazole-containing dyes, since these compounds were found to have high light stability, mainly due to their effective UV absorbance (See, for example, B. I. Stepanov, Introduction to the Chemistry and Technology of Organic Dyes, publ. "Chemistry", Moscow, 1977, p. 253–268).

Examples of light stabilizers based on pyrazole derivatives and their metal salts or metal complexes are disclosed in Ger. Pat. No. 2,433,111; 2,410,370; 2,519,594; 2,651,272; 2,529,052; and 2,511,354, Fr. Pat. No. 2,777,826, U.S. Pat. No. 4,008,200, Swiss Pat. No. 605,796, Belg. Pat. No. 891,814, and S.U. Pat. Nos. 956,504; 737,401; 2,829,024; 1,427,802; 1,015,664; 1,205,543; 1,005,448; 717,043; and 786,317.

However, most of these light stabilizers do not exhibit efficient radical scavenging activity, and they lose their effectiveness under condiotions of continuous and intensive irradiation.

There is thus a widely recognized need for, and it would be highly advantageous to have, a light stabilizer which incorporates the effective UV absorption of pyrazole derivatives and the efficient radical scavenging activity of hindered amine light stabilizers (HALS) such as piperidine derivatives, and which retains its effectiveness under conditions of continuous and intensive irradiation.

SUMMARY OF THE INVENTION

According to the present invention there is provided a novel chemical compound useful as a light stabilizer for polymers such as polyesters, polystyrene, polycarbonate, and polyolefins, comprising: (a) a pyrazole derivative; and (b) a piperidine derivative.

Also according to the present invention, there is provided a metal complex comprising: (a) a chemical compound, including: (i) a pyrazole derivative; and (ii) a piperidine derivative; and (b) a metal ion.

Further according to the present invention, there are provided methods for the synthesis of the metal complex, including (a) reaction of the chemical compound with metal acetate; or (b) reaction of a metal complex with a suitable derivative.

According to further features in preferred embodiments of the invention described below, the pyrazole derivative may be a 4-aminomethylene derivative of 2-pyrazolin-5-one or 2-pyrazolin-5-thione.

The pyrazole derivative may further be a derivative of 5-aminopyrazole, and may be substituted at its 4-position with CH=O, or CH=N-Aryl such as CH=NC$_6$H$_5$, CH=NC$_6$H$_4$OC$_6$H$_5$, CH=NC$_6$H$_4$COOC$_4$H$_9$ (m- or p-), and CH=NC$_6$H$_2$[p-OH,m,m'-C(CH$_3$)$_3$].

Further, the pyrazole derivative may be substituted with a phenyl group at its 1-position and a methyl group at its 3-position.

According to still further features in the described preferred embodiments, the piperidine derivative may be a 2,2',6,6'-tetramethylpiperidine derivative, and may further be substituted at its 1-position with alkyl such as methyl, a carboxyacryloyl derivative such as 3-carboxyacryloyl and 2-carboxymethylacryloyl, a carboxybenzoyl derivative such as 2-carboxybenzoyl, and a pyrazole derivative such as 3-Me-1-Ph-5-pyrazolonylmethylidene-4, and 3-Me-1-Ph-5-thiopyrazolonylmethylidene-4.

The metal complex may include a metal ion such as Ni(II), Zn(II), Cu(II), and Co(II).

The reaction of the chmical compound with a metal acetate may be carried out in ethanol or acetone. The reaction of a metal complex with a suitable derivative may be carried out in a benzene solution. The suitable derivative may be anhydride or a pyrazole derivative.

The present invention successfully addresses the shortcomings of the presently known configurations by providing a chemical compound useful as a light stabilizer, which incorporates the properties of an effective UV absorber such as a pyrazole derivative, and an efficient radical scavenger such as a piperidine derivative, and which retains its effectiveness under conditions of continuous and intensive irradiation.

Further, the present invention provides high molecular mass and highly compatible metal complexes of such chemical compounds, which incorporate the properties of UV absorbers, radical scavengers, hydroperoxide decomposers, and excited state quenchers, and which therefore feature considerable photostability and thermostability.

The present invention discloses a novel chemical compound useful as a light stabilizer which incorporate a pyrazole derivative and a piperidine derivative, metal complexes of such chemical compound, and methods for the synthesis of such metal complexes. The chemical compounds and their metal complexes may be used as additives to polymers such as polyesters, polystyrene, polycarbonate and polyolefins. They may be added to a melted polymer by conventional mixing or blending techniques, or may be dissolved in a suitable solvent and added to the polymer as a solution.

BRIEF DESCRIPTION OF THE DRAWINGS

The invention is herein described, by way of example only, with reference to the accompanying drawings, wherein:

FIG. 2b represents specific examples of metal complexes which can be synthesized according to the method illustrated in FIG. 2a.

FIG. 3b represents specific examples of metal complexes which can be synthesized according to the methods illustrated in FIGS. 2a and 3a.

DESCRIPTION OF THE PREFERRED EMBODIMENTS

The present invention is of a chemical compound which can be used as a light stabilizer for various polymers, and which incorporates the properties of an effective UV absorber such as a pyrazole derivative, and an efficient radical scavenger such as a piperidine derivative. Further, the invention is of a metal complex of such compound, and methods for the synthesis of such a metal complex.

Examples of available commercial hindered amine light stabilizer (HALS) which are based on piperidine derivatives are Tinuvin 770, Tinuvin 622, Tinuvin 292, and Chimassorb 994. The stabilizing mechanism of such compounds is described in detail in the literature (see, for example, G. Scott, "Atmospheric Oxidation and Antioxidants", Elsevier, A-L-NY-T, Vol 1,2,3, 1993), and is based on a catalytic cycle in which there is a continuous feedback of piperidinoxyl radicals which react with alkyl radicals to produce: (a) non-radical products such as olefins; and (b) hydroxylamines which are known to be effective light stabilizers. Thus, such compounds renew their radical-scavenging capabilities due to continuous decomposition and formation of piperidinoxyl radicals and hydroxylamines, and are therefore very effective light stabilizers. The incorporation of an effective UV absorber such as a pyrazole derivative and an efficient radical scavenger such as a piperidine derivative in a single compound results in a synergistic behaviour, in which the overall stabilizing effect of the pyrazole-piperidine combination is greater than the sum of the stabilizing effects of the individual components (pyrazole alone and piperidine alone), since the pyrazole protects the piperidine from destruction by UV light, and the piperidine inhibits the formation of alkyl radicals and therefore extends the useful life of the pyrazole.

Thus, compounds according to the present invention have high extinction coefficient in the region of 250–360 nm, and they show high light-stability under conditions of continuous and intensive irradiation such as Hg Lamp (400 W) and sunlight (Summer, Ashkelon, Israel). Furthermore, several embodiments are thermostable up to 300° C. In addition, compounds according to the present invention show high solubility in most organic solvents and high compatibility with various polymers such as polyesters, polystyrene, polycarbonate, and polyolefins.

Metal complexes of compounds according to the present invention incorporate the properties of UV-absorbers, free radical scavengers, hydroperoxide decomposers, and excited state quenchers. Further, they have high molecular mass and therefore are not volatile. As a result, these metal complexes exhibit spectral properties which are similar to those of the individual compounds they are built of; however, they show much higher photostability and thermostability.

Methods for the synthesis of metal complexes according to the present invention enable the extraction of high yields of products by using simple and inexpensive technology.

The principles and operation of the present invention may be better understood with reference to the drawings and the accompanying description.

Figure 1A:
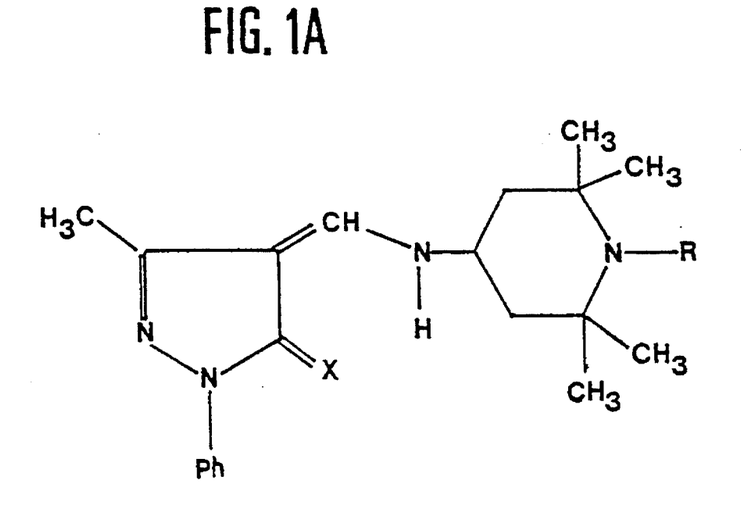
FIG. 1a represents the chemical structure of a compound according to the present invention, in which the pyrazole derivative is 4-aminomethylene-2-pyrazolin-5-one or -thion.
Figure 1B:
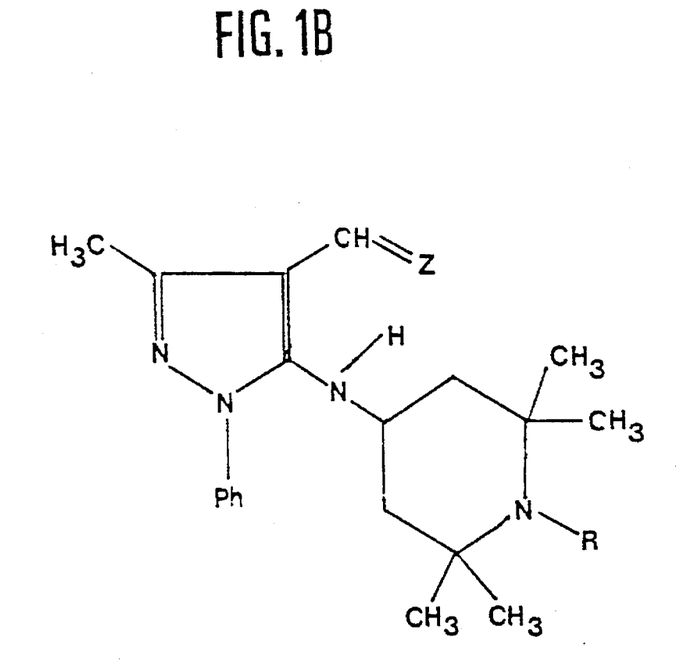
FIG. 1b represents the chemical structure of an alternative compound according to the present invention, in which the pyrazole derivative is a substituted 5-aminopyrazole.

Referring now to the drawings, FIGS. 1a, and b illustrate the chemical structure of a compound according to the present invention. The compound includes a pyrazole derivative and a piperidine derivative.

As shown in FIG. 1a, the pyrazole derivative may be a 4-aminomethylene derivative of 2-pyrazolin-5-one or 2-pyrazolin-5-thione, and may preferably be substituted with a phenyl group at its 1-position and a methyl group at its 3-position.

The piperidine derivative may preferably be 2,2',6,6'-tetramethylpiperidine, and may be substituted at its 1-position with substituents such as: (a) alkyl such as methyl; (b) a carboxyacryloyl derivative such as 3-carboxyacryloyl and 2-carboxymethylacryloyl; (c) a carboxybenzoyl derivative such as 2-carboxybenzoyl; and (d) a pyrazole derivative such as 3-Me-1-Ph-5-pyrazolonylmethylidene-4, and 3-Me-1-Ph-5-thiopyrazolonylmethylidene-4.

Another possible configuration is shown in FIG. 1b, wherein the pyrazole derivative may be a derivative of 5-aminopyrazole, and may be substituted at its 4-position with substituents such as CH=O, or CH=N-Aryl such as $CH=NC_6H_5$, $CH=NC_6H_4OC_6H_5$, $CH=NC_6H_4COOC_4H_9$ (m- or p-), and $CH=NC_6H_2[p-OH,m,m'-C(CH_3)_3]$.

With continued reference to FIGS. 1a, and b, the chemical compounds may be synthesized according to methods described in the literature (see, for example, I. Y. Kvitko, J. Org. Khim. 34, 2999–3005 (1964); I. Y. Kvitko, J. Org. Khim. 1, 169–173 (1966); and I. Y. Kvitko, J. Org. Khim. 5, 1685–92 (1969).

Figure 1C:
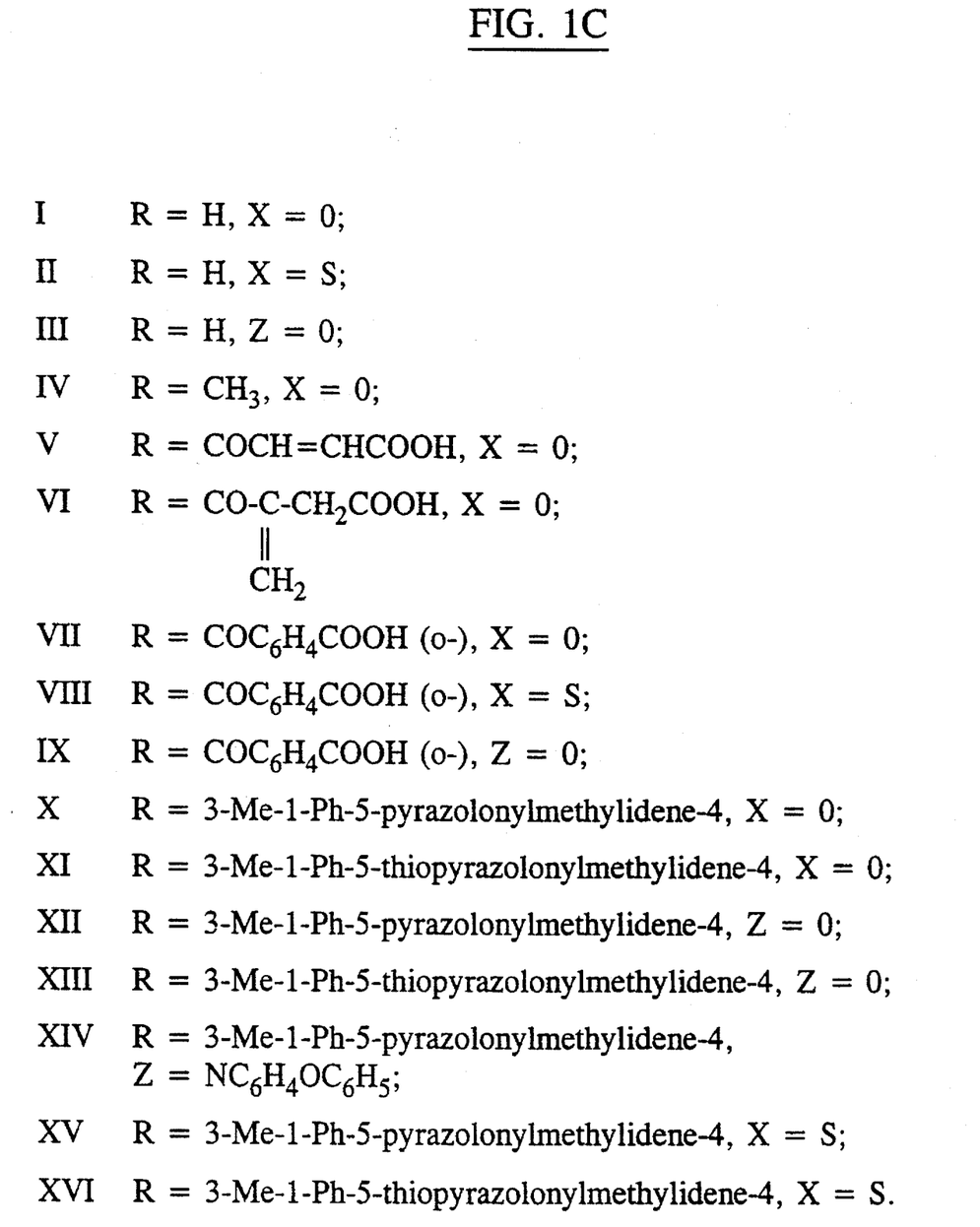
FIG. 1c represents specific examples of the compounds shown in FIGS. 1a and b.

FIG. 1c represents specific examples of the compounds shown in FIGS. 1a and b. Compounds I–IV may preferably be synthesized by reacting the corresponding 3-methyl-1-phenyl-5-hydroxy(mercapto- or chloro-)pyrazolecarboxylaldehydes with 4-amino-2,2',6,6'-tetramethylpiperidine or 4-amino-1,2,2',6,6'-pentamethylpiperidine. Compounds V–IX may preferably be synthesized by reacting compounds I, II or III, with maleic, itaconic, or phtalic anhydride in benzene solution. Compounds X–XVI may preferably be synthesized by reacting compounds I, II or III, with 3-methyl-1-phenyl-5-hydroxy-4-formylpyrazole or 3-methyl-1-phenyl-5-mercapto-4-formylpyrazole. This reaction may preferably be carried out in benzene solution, at 40°–60° C., for about 30 min.

Figure 2A:
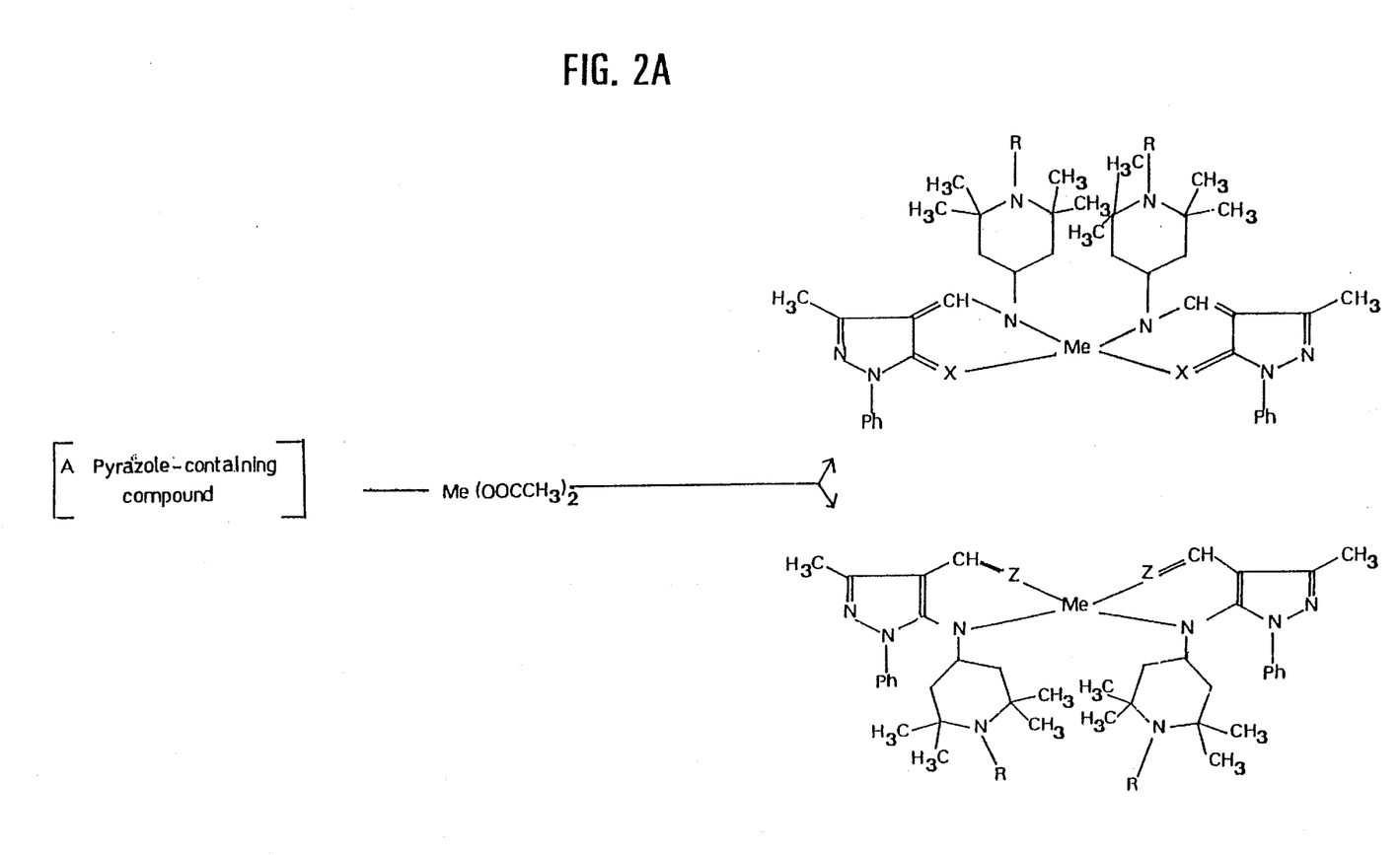
FIG. 2a represents the chemical structure of metal complexes of the compounds shown in FIGS. 1a, b and c, and a schematic description of a method for the synthesis of such metal complexes.

FIG. 2a illustrates the chemical structure of metal complexes of the compounds shown in FIGS. 1a, b, and c. The metal complexes may include metal ions such as Ni(II), Zn(II), Cu(II), and Co(II).

Further, FIG. 2a shows a schematic description of a method for the synthesis of such metal complexes. Thus, the metal complex may preferably be synthesized by reacting a compound such as in FIGS. 1a, b, and c, with the corresponding metal acetate $Me(OOCCH_3)_2$, in ethanol or acetone.

Figure 2B:
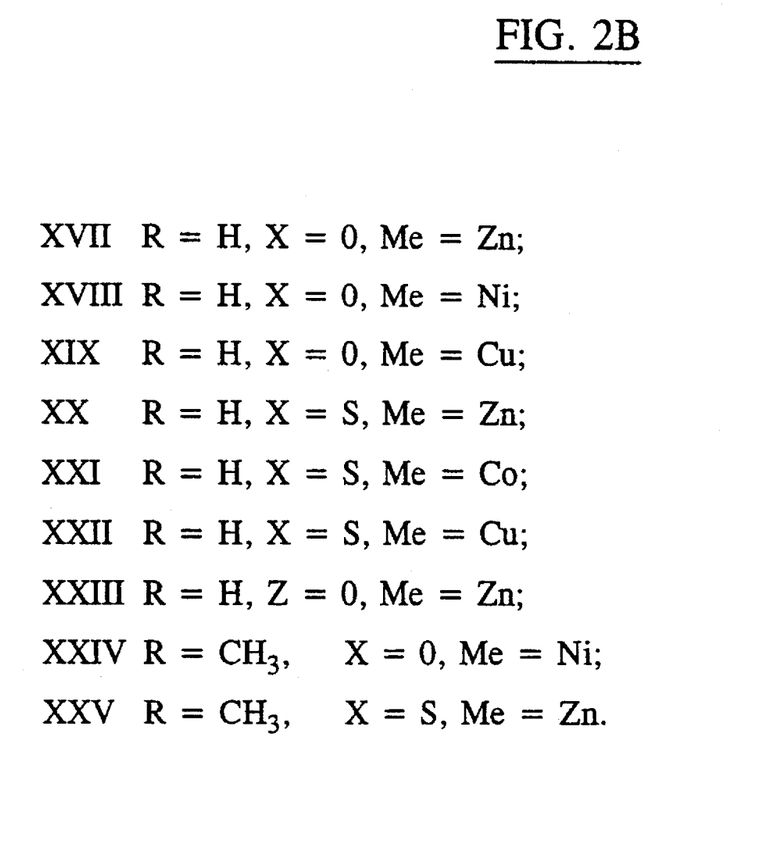
Figure 3A:
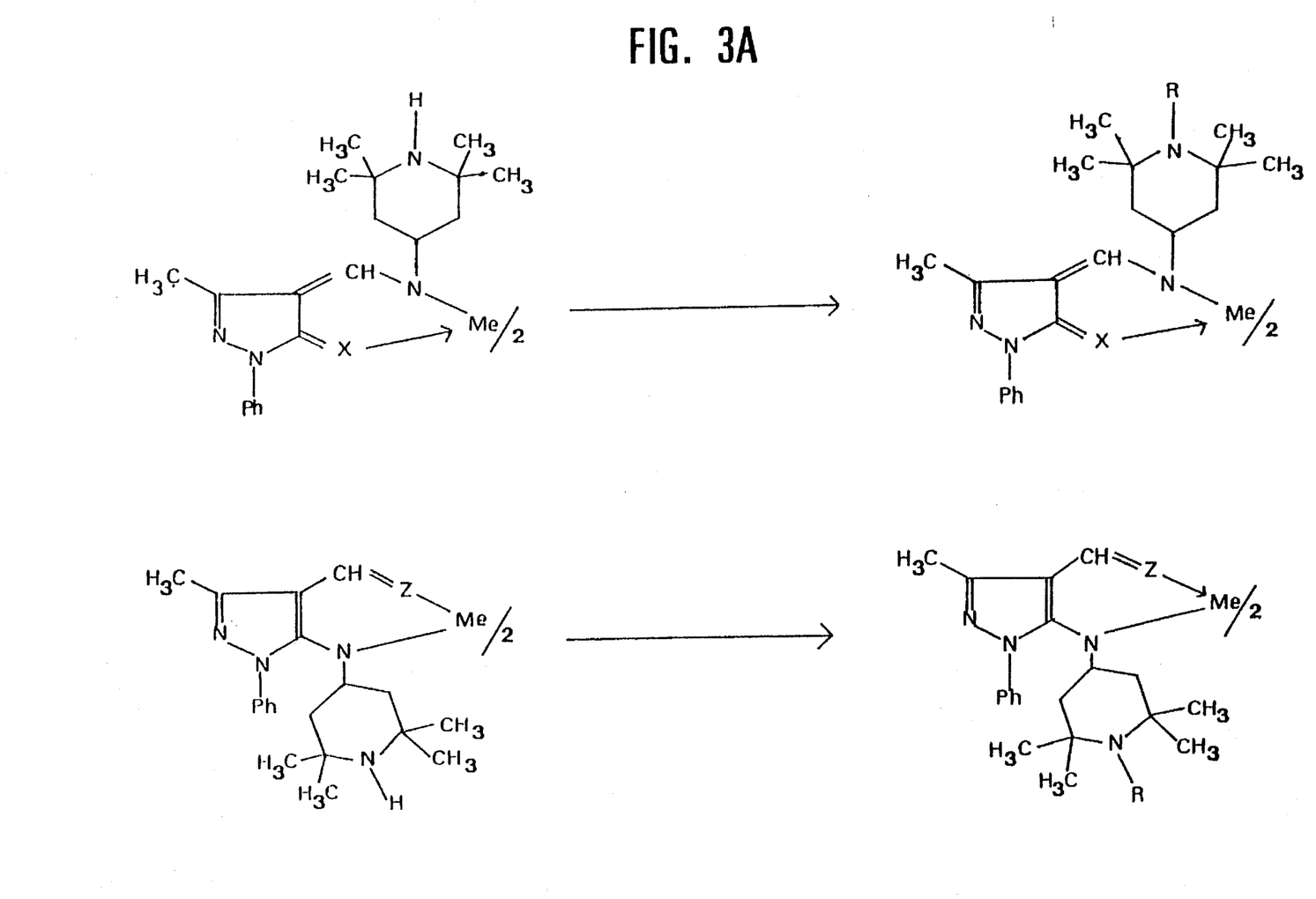
FIG. 3a is a schematic description of an alternative method for the synthesis of some of the metal complexes.
Figure 3B:
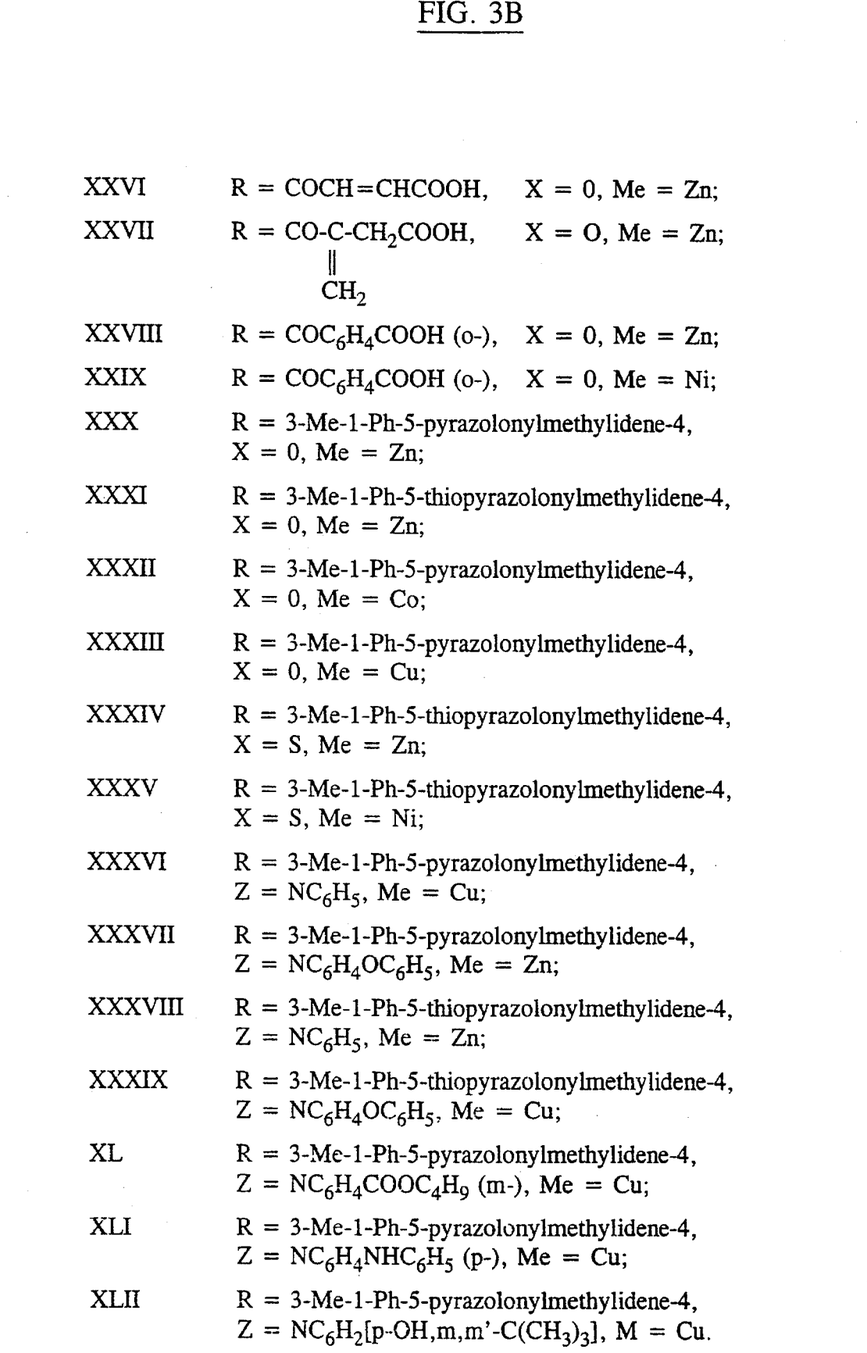

Specific examples of metal complexes which can be synthesized according to the method illustrated in FIG. 2a are given in FIGS. 2b and 3b, where compounds XVII–XXV are metal complexes of compounds I–IV in FIG. 1c, and compounds XXVI–XLII are metal complexes of compounds V–XVI in FIG. 1c.

FIG. 3a represents an alternaive method for the synthesis of a metal complex of a compound in which the piperidine derivative is substituted with, for example, a derivative of carboxyacryloyl, carboxybenzoyl, or pyrazole. Such metal complex may preferably be synthesized by reacting a metal complex of a compound in which the piperidine derivative is unsubstituted or substituted with, for example, $CH_3$, with the corresponding anhydride or pyrazole derivative. This reaction may preferably be carried out in benzene solution at room temperature.

Specific examples of metal complexes which can be synthesized according to the method illustrated in FIG. 3a are given in FIG. 3b. Thus, compounds XXVI–XLII may be synthesized by reacting compounds XVII–XXV, which are metal complexes of compounds I–IV in FIG. 1c, with the corresponding anhydride or pyrazole derivative as mentioned above.

Referring now to the examples, the preparation and the resulted photostabilizing activities of compounds and metal complexes according to the present invention are described.

The photostabilizing activities were evaluated using UV-spectrophotometer, in ethanolic, chloroformic and isooctanic solutions. The absorption of compounds and metal complexes was measured before and after irradiation by: (a) a Hg Lamp (400 W) for a period of 1–5 hours; (b) sunlight (summer, Ashkelon, Israel) for a period of about 10 days; and (c) a weathermeter (standard conditions) for 250 hours.

EXAMPLE 1

3-Methyl-1-phenyl-4-(2,2',6,6'-tetrammethylpiperidyl-4)amino-methylen-5-pyrazolinon (Compound I, FIG. 1c)

To a 1 l kettle equipped with a mixer, condenser, and a bath for heating, were added: 500 ml of benzene; and 229 g of 3-methyl-1-phenyl-4-dimethylaminomethylene-5-pyrazolon which were obtained with a yield of 92% from 3-methyl-1-phenyl-5-pyrazolone, dimethylformamideand-phosphoryltrichloride, using the method described in J. Ob. Khim. 32, 4050–4056 (1962).

To the resulting suspension, 187 g (202 ml) of 4-amino-2,2',6,6'-tetramethylpiperidine, obtained by "Fluka", were added by mixing over a period of 10–20 min, at room temperature. The mixture was then refluxed for 12 hours. The dimethylamine formed in the condenser was sent for abosrption in a vessel containing cold water. After heating, some of the benzene (~250 ml) was distilled, and the residue was transferred to a crystallizator. After cooling at room temperature (~10–12 hours), the crystalline product was filtered and washed on the filter with 250 ml of petroleum ether.

The result was 285 g of yellowish crystals with a m.p. of 135°–137° C. From the benzene-petroleum ether mixture, 41.4 g with a m.p. of 132°–134° C. were obtained. The total yield was 326.4 (96%). After crystallization from n-hexane, the m.p. was 136°–137° C. Point of decomposition >290° C. The product dissolves in ethanol, methanol, chloroform, dichloromethane, benzene, acetone, n-hexane, and diethylether, and with difficulty in petroleum ether and water. λmax in ethanol: 330; 295; and 255 nm. Found %: C 70.45; H 7.99; N 16.32. Gross formula: $C_{20}H_{28}N_4O$. Calc. %: C 70.6; H 8.23; N 16.32.

The absorption results obtained before (d) and after (d') irradiation by Hg Lamp (400 W), at 50° C., for 1 hour, at a distance of 50 cm:

| λmax | 330 | 295 | 255 |
| --- | --- | --- | --- |
| d | 0.5 | 2.0 | 1.35 |
| d' | 0.45 | 1.9 | 1.30 |

The absorption results obtained before (d) and after (d') irradiation by sunlight, in ethanol solution ($5·10^{-5}$), for 7 days, in the conditions of May 1995, Ashkelon:

| λmax | 330 | 295 | 255 |
|---|---|---|---|
| d | 0.5 | 2.0 | 1.35 |
| d' | 0.48 | 1.97 | 1.24 |

The results of colour estimation according to Hardners methods before and after irradiation of a polyester plate (3 mm) in a weathermeter for 250 hours: Before: 2; After 250 hours: 1.

EXAMPLE 2

3-Methyl-1-phenyl-4-(2,2',6,6'-tetramethylpiperidyl-4)aminomethylen-5-thiopyrazolinon (Compound II, FIG. 1c)

This compound was obtained from 3-methyl-1-phenyl-4-methylaminomethylene-5-thiopyrazolinone, which was synthesized with a yield of 91% using the method of Kvitko I. Y. (J. Org. Khim. 5, 1685–9), and 4-amino-2,2',6,6'-tetramethylpiperidine, as in example 1.

The compound was obtained with a yield of 94%. The m.p. was 210°–212° C. After crystallization from toluene the m.p. was 212°–213° C. Point of decomposition >260° C.

This product dissolves in ethanol, methanol, chloroform, dioxane, acetone, benzene, and toluene, and by heating, in diethylether and n-hexane. However, it does not dissolve in petroleum ether. λmax in ethanol: 385, 300, 280, and 235 nm. Found %: C 67.15; H 7.91; N 15.48; S 9.14. Gross Formula: $C_{20}H_{28}N_4S$. Calc %: C 67.4; H 7.9; N 15.7; S 8.9.

The absorption results obtained before (d) and after (d') irradiation by Hg Lamp (400 W), at 50° C., for 1 hour, at a distance of 50 cm:

| λmax | 385 | 300 | 280 | 235 |
|---|---|---|---|---|
| d | 0.605 | 1.933 | 2.06 | 1.49 |
| d' | 0.3 | 1.4 | 1.46 | 1.09 |

EXAMPLE 3

3-Methyl-1-phenyl-5-(2,2',6,6'-tetramethylpiperidyl-4)aminopyrazole-4-carboxylaldehyde (Compound III, FIG. 1c)

To a 1 l kettle equipped with a mixer, thermometer, and a bath for heating, were added: 220.5 g of 3-methyl-1-phenyl-5-chloropyrazole-4-carboxyaldehyde obtained by method described in J. Org. Khim 1966, 1, 169–173; 300 ml of dimethylformamide; and 234 g of 4-amino-2,2',6,6'-tetramethylpiperidine.

The mixture was heated at 95°–100° C. for 8 hours. After heating the solution was transferred to a crystallizator containing 1,200 ml of water. After cooling to room temperature by mixing, the pale yellow precipitate was filtered, washed with cold water (3×50 ml) and air-dried. 289 g (85%) of colourless product were obtained with a m.p. of 78°–82° C. After crystallization from an ethanol-water mixture and subsequently from petroleum ether, the m.p. was 95°–96° C. and the point of decomposition >300° C.

This product dissolves in most organic solvents, and does not dissolve in water. λmax in ethanol: 260 nm; in isooctane: 265 nm.

The absorption results obtained before (d) and after (d') irradiation by Hg Lamp (400 W), at 50° C., for 1 hour, at a distance of 50 cm, in isooctan solution:

| λmax | 260 |
|---|---|
| d | 2.05 |
| d' | 1.98 |

EXAMPLE 4

3-Methyl-1-phenyl-4(1,2,2',6,6'-pentamethylpiperidyl-4)aminomethylen-5-pyrazolinon (Compound IV, FIG. 1c)

A 250 ml one-necked round bottom flask, equipped with condenser and magnetic stirrer, was filled with 46 g of 3-methyl-1-phenyl-4-dimethylaminomethylene-5-pyrazolinone (see example 1 ), 100 ml of benzene and 38 g of 4-amino-1,2,2',6,6'-pentamethylpiperidine. The mixture was refluxed for 8 hours.

After cooling the precipitate was collected by filtration, washed on the filter with petroleum ether, and dried. 64 g (91%) of pale yellow product was obtained, with a m.p. of 153°–154° C. After crystallization from benzene the m.p. was 155°–156° C.

This compound has good solubility in most organic solvents, and does not dissolve in petroleum ether and water. λmax in ethanol: 330, 298, and 255 nm. Found %: C 71.46; H 8.56; N 15.64. Gross formula: $C_{21}H_{30}N_4O$. Calc %: C 71.2; H 8.48; N 15.82.

The absorption results obtained before (d) and after (d') irradiation by Hg Lamp (400 W), at 50° C., for 1 hour, at a distance of 50 cm, in ethanolic solution:

| λmax | 330 | 298 | 255 |
|---|---|---|---|
| d | 0.65 | 1.92 | 1.65 |
| d' | 0.60 | 1.90 | 1.60 |

EXAMPLE 5

Compounds V–XIV, FIG. 1c (A) 3-Methyl-1-phenyl-4(1-(3'-carboxyacryloyl)-2,2',6,6'-tetramethylpiperidyl-4)aminomethylene-5-pyrazolinone (Compound V, FIG. 1c)

A 250 ml one-necked round bottom flask, equipped with condenser and magnetic stirrer, was filled with 34 g of 3-methyl-1-phenyl-4-(2,2',6,6'-tetramethylpiperidyl-4)amino-methylene-5-pyrazolinone (I), and 100 ml of benzene. After dissolving the residue, the solution was cooled at 0°–5° C., and 10 g of maleic anhydride was added by mixing. The mixture was kept at these conditions for 3 hours and was left for 12 hours at room temperature.

The precipitate was collected by filtration, washed with 50 ml of petroleum ether and dried. 41 g (93%) of pale yellow powder was obtained, with a m.p. of 244°–246° C. After crystallization from toluene the m.p. was 246°–247° C., and the molecular mass was 438. Point of decomposition: 250° C. λmax in ethanol: 300 and 258 nm.

(B) Compounds VI–IX, FIG. 1c

Compounds VI–IX were obtained using the same procedure as in (A), with the following yield, molecular mass, m.p., and λmax:

3-methyl-1-phenyl-4-[1-(3'-carboxylmethylacryloyl)-2,2',6,6'-tetramethylpiperidyl-4]aminomethylene-5-pyrazolinone (VI):92%, 452, 212°–214° C., λmax (ethanol) 300, 255 nm;

3-methyl-1-phenyl-4-[1-(o-carboxybenzoyl)-2,2',6,6'-tetramethylpiperidyl-4]aminomethylene-5-pyrazolinone (VII): 92.5%, 488, 223°–225° C., λmax (ethanol) 298, 260 nm;

3-methyl-1-phenyl-4-[1-(o-carboxybenzoyl)-2,2',6,6'-tetramethylpiperidyl-4]aminomethylene-5-thiopyrazolinone (VIII): 68%, 504, 227°–230° C. (decomp.), λmax (ethanol) 380, 300, 280, 235 nm;

3-methyl-1-phenyl-5-[1-(3'-carboxyacryloyl)-2,2',6,6'-tetramethylpiperidyl-4]aminopyrazole methylene-4-carboxyaldehyde (IX): 92%, 438, 193°–195° C. (benzene), 270° C., λmax (ethanol) 262 nm.

(C) Compounds X–XVI, FIG. 1c

Compounds X–XVI were obtained using the same procedure, but the reaction with carboxyaldehydes was carried out by heating at 40°–60° C. The pertinent yield, molecular mass, m.p., point of decomp., and λmax are:

3-methyl-1-phenyl-4-[1-(3'-methyl-1'-phenyl-5'-pyrazolonylmethylidene-4)-2,2',6,6'-tetramethylpiperidyl-4]aminomethylene-5-pyrazolinone (X): 96%, 524, 225°–226° C. (toluene), 260° C., λmax (ethanol) 295, 260 nm; (CHCl₃) 298, 255 nm;

3-methyl-1-phenyl-4-[1-(3'-methyl-1'-phenyl-5'-thiopyrazolonylmethylidene-4)-2,2',6,6'-tetramethylpiperidyl-4]aminomethylene-5pyrazolinone (XI): 93.5%, 540, 208°–210° C. (dioxane), >240° C., λmax (ethanol) 295, 265, 230 nm; (CHCl₃) 298, 275 nm;

3-methyl-1-phenyl-5-[1-(3'-methyl-1-phenyl-5-pyrazolonylmethylidene-4')-2,2',6,6'-tetramethylpiperidyl-4]aminopyrazole-4-carboxyaldehyde (XII): 83.5%, 524, 208°–209° C. (benzene), >230° C., λmax (ethanol) 260 nm;

3-methyl-1-phenyl-5-[1-(3'-methyl-1-phenyl-5-thiopyrazolonylmethylidene-4')-2,2',6,6'-tetramethylpiperidyl-4]aminopyrazole-4-carboxyaldehyde (XIII): 92.8%, 540, 245°–247° C. (toluene), >260° C., λmax (ethanol) 280, 225 nm;

3-methyl-1-phenyl-5-[1-(3'-methyl-1-phenyl-5-pyrazolonylmethylidene-4')-2,2',6,6'-tetramethylpiperidyl-4]aminopyrazole-4-carboxy (ald(p-phenoxy)phenylimin (XIV): 58%, 152°–154° C. (benzene), λmax (ethanol) 325, 260, 250 nm;

3-methyl-1-phenyl-4-[1-(3'-methyl-1-phenyl-5-pyrazolonylmethylidene-4')-2,2',6,6'-tetramethylpiperidyl-4]aminomethylene-5-thiopyrazolinone (XV): 96%, 540, 215°–217° C. (toluene), >250° C., λmax (ethanol) 380, 300, 260 nm;

3-methyl-1-phenyl-4-[1-(3'-methyl-1-phenyl-5-thiopyrazolonylmethylidene-4')-2,2',6,6'-tetramethylpiperidyl-4]aminomethylene-5-thiopyrazolinone (XVI): 94%, 556, 245°–246° C. (dioxane), 250° C., λmax (ethanol) 380, 300, 265 nm.

(D) Data of absorption of the ethanolic solutions of compounds V–XVI (FIG. 1c)

The data of absorption obtained for the ethanolic solutions of compounds V–XVI at the corresponding λmax values, before (d) and after (d') irradiation by Hg Lamp (400 W), at 50° C.:

| Compound | λmax (d) | λ'max (d') |
|---|---|---|
| V | 300 (1.45), 258 (1.28) | 300 (1.42), 258 (1.25) |
| VI | 300 (1.62), 255 (1.46) | 300 (1.60), 255 (1.40) |
| VII | 298 (1.38), 260 (1.22) | 298 (1.36), 260 (1.20) |
| VIII | 380 (0.60), 300 (1.28) 280 (1.50), 235 (1.65) | 380 (0.20), 300 (1.50) 280 (0.85), 235 (1.50) |
| IX | 262 (1.25) | 262 (1.20) |
| X | 295 (1.16), 265 (1.67) | 295 (1.10), 265 (1.58) |
| XI | 265 (1.40), 230 (1.55) | 265 (1.35), 230 (1.50) |
| XII | 260 (1.75), 230 (1.60) | 260 (1.70), 230 (1.50) |
| XIII | 280 (1.65), 260 (1.50) | 280 (1.35), 260 (1.60) |
| XIV | 340 (1.25), 260 (1.10) 230 (1.40) | 340 (1.20), 260 (1.10) 230 (1.35) |
| XV | 380 (0.65), 300 (1.40) 260 (1.35) | 380 (0.25), 300 (0.85) 260 (1.40) |
| XVI | 380 (0.60), 300 (1.45) 265 (1.20) | 380 (0.25), 300 (0.90) 265 (1.20) |

EXAMPLE 6

Compounds XVII–XXXI, FIGS. 2b and 3b (A) Zinc bis [3-Methyl-1-phenyl-4-(2,2',6,6'-tetramethylpiperidyl-4) aminomethylene-5-pyrazolonate (compound XVII, FIG. 2b)

170 g of 3-methyl-1-phenyl-4-(2,2',6,6'-tetramethylpiperidyl-4) aminomethylene-5-pyrazolinone (I) and 300 ml of acetone were added to a 1 l kettle equipped with a mixer, condenser, and bath for heating and cooling. The resulting solution was heated to 50° C. and a solution of 57 g of zinc acetate dihydrate in 150 ml of water was added to it. The mixture was heated at this temperature for 30 min, and then cooled to room temperature.

After 3 hours the precipitate was collected by filtration. The precipitate was placed in a 3 l glass equipped with a mixer, and 1 l of cold water (15°–20° C.) was added to it. To this suspension, a solution of 26 g of sodium carbonate in 200 ml of water was added, over a period of 2 hours. After neutralization of the acetic acid, the precipitate was collected by filtration, washed with 150 ml of cold water (~10° C.) and dried at 60°–70° C.

The complex was obtained with a yield of 172 g (92.4%) of colourless powder, with a m.p. of 236°–239° C. After crystallization from benzene the m.p. was 248°–249° C. This complex dissolves well in methanol, ethanol, chloroform, toluene, acetone, and dioxane. When heated it dissolves in n-hexane, and partly in petroleum ether. λmax (ethanol): 295 and 255 nm. Found %: C 64.25; H 7.14; N 15.28. Gross formula: $C_{40}H_{54}N_8O_2Zn$. Calc. %: C 64.60; H 7.27; N 15.09

The absorption results obtained before (d) and after (d') irradiation by sunlight for a period of 7 days under conditions of June, 1995, Ashkelon, Israel, in ethanolic solution (5·10⁻⁵):

| λmax | 295 | 255 |
|---|---|---|
| d | 1.56 | 1.28 |
| d' | 1.52 | 1.20 |

The absorption results obtained before (d) and after (d') irradiation by Hg Lamp (400 W), at 50° C., for 1 hour, in ethanol solution:

| λmax | 295 | 255 |
|------|------|------|
| d    | 1.78 | 1.48 |
| d'   | 1.72 | 1.47 |

The results of colour estimation according to Hardners method before and after irradiation of a polyester plate (3 mm) in a weathermeter for 250 hours: Before: 1; After 250 hours: 1.

(B) Compounds XVIII–XXVII, FIGS. 2b and 3b

Complexes XVIII–XXVII were obtained by the same procedure as in (A), with the following yield, gross formula and molecular mass, m.p., point of decomp., and λmax:

Nickel bis[3-methyl-1-phenyl-4-(2,2',6,6'-tetramethylpiperidyl-4)-aminomethylene-5-pyrazolonate]dihydrate (XVIII): 90.5%, $C_{40}H_{54}N_8O_2Ni\cdot 2H_2O$, 772, 236°–238° C. (benzene), >280° C., λmax (EtOH) 300, 275, 260 nm;

Copper bis[3-methyl-1-phenyl-4-(2,2',6,6'-tetramethylpiperidyl-4)-aminomethylene-5-pyrazolonate] (XIX): 92.3%, $C_{40}H_{54}N_8O_2Cu$, 741, 206°–208° C. (benzene), >270° C.;

Zinc bis[3-methyl-1-phenyl-4-(2,2',6,6'-tetramethylpiperidyl-4)-aminomethylene-5-thiopyrazolonate] (XX): 90.5%, $C_{40}H_{54}N_8S_2Zn$, 775, 252°–254° C. (toluene), >290° C., λmax (ethanol) 330, 285, 260, 225 nm;

Cobalt bis[3-methyl-1-phenyl-4-(2,2',6,6'-tetramethylpiperidyl-4)-aminomethylene-5-thiopyrazolonate]dihydrate (XXI): 86%, $C_{40}H_{54}N_8S_2Ni\cdot 2H_2O$, 768.7, 245°–247° C. (toluene), >290° C., λmax (ethanol) 340, 300, 280, 240 nm;

Copper bis[3-methyl-1-phenyl-4-(2,2',6,6'-tetramethylpiperidyl-4)-aminomethylene-5-thiopyrazolonate] (XXII): 91.5%, $C_{40}H_{54}N_8S_2Cu$, 773, 236°–237° C. (benzene), >290° C., λmax (ethanol) 330, 290, 260, 230 nm;

Zinc bis[3-methyl-1-phenyl-5-(2,2',6,6'-tetramethylpiperidyl-4)-4-carboxyaldehyde-5-aminopyrazolonate] (XXIII): 85.6%, $C_{40}H_{54}N_8O_2$, 743, 198°–199° C. (benzene-n-hexane), >290° C., λmax (ethanol) 260, 235 nm;

Nickel bis[3-methyl-1-phenyl-4-(1,2,2',6,6'-pentamethylpiperidyl-4)-aminomethylene-5-pyrazolonate]dehydrate (XXIV): 89.8%, $C_{42}H_{58}N_8O_2Ni\cdot 2H_2O$, 800.7, 242°–243° C. (benzene), >280° C., λmax (ethanol), 280 nm.

Zinc bis[3-methyl-1-phenyl-4-(1,2,2',6,6'-pentamethylpiperidyl-4)-aminomethylene-5-thiopyrazolonate] (XXV): 90.6%, $C_{42}H_{58}N_8S_2Zn$, 803, 256°–258° C. (benzene), >290° C., λmax (ethanol) 330, 288, 260, 237 nm.

Data of Absorption of the Ethanolic and Isooctanic Solutions of Compounds XVII–XXXI, FIGS. 2b and 3b The data of absorption obtained for the ethanolic and isooctanic solutions of compounds XVII–XXXI at the corresponding λmax values, before (d) and after (d') irradiation by Hg Lamp (400 W) at 50° C. for 1 hour at a distance of 50 cm:

|       | Ethanol     |             | Isooctane   |             |
|-------|-------------|-------------|-------------|-------------|
| Comp. | λmax (d)    | λmax (d')   | λmax (d)    | λmax (d')   |
| XVII  | 295 (1.55)  | 295 (1.50)  | 298 (1.70)  | 298 (1.65)  |
|       | 255 (1.28)  | 255 (1.20)  | 258 (1.30)  | 258 (1.60)  |
| XVIII | 300 (1.10)  | 300 (1.00)  | 305 (1.20)  | 305 (1.00)  |
|       | 275 (1.85)  | 275 (1.70)  | 275 (1.90)  | 275 (1.50)  |
| XIX   | 280 (1.649) | 280 (1.10)  |             |             |
|       | 260 (1.555) | 260 (1.28)  |             |             |
| XXVI  | 295 (1.65)  | 295 (1.60)  | 295 (1.70)  | 295 (1.65)  |
|       | 255 (1.30)  | 260 (1.28)  | 255 (1.35)  | 255 (1.30)  |
| XXVIII| 295 (1.65)  | 295 (1.60)  | 298 (1.70)  | 298 (1.65)  |
|       | 255 (1.55)  | 255 (1.45)  | 255 (1.60)  | 255 (1.55)  |
|       | 230 (1.35)  | 230 (1.35)  |             |             |
| XXX   | 310 (0.75)  | 310 (0.60)  |             |             |
|       | 280 (1.85)  | 280 (1.50)  |             |             |
|       |             | 220 (1.30)  |             |             |
| XXXI  | 305 (0.95)  | 305 (0.85)  |             |             |
|       | 270 (1.55)  | 270 (1.50)  |             |             |
|       | 225 (1.35)  | 225 (1.30)  |             |             |
| Tin 320 | 348 (1.25) | 348 (1.25) | 348 (1.30)  | 348 (1.25)  |
|       | 300 (1.20)  | 300 (1.15)  | 300 (1.20)  | 300 (1.10)  |

The absorption data for Tinuvin 320 are given for comparison.

EXAMPLE 7

Compounds XXVI–XXXV (FIG. 3b)

(A) Zinc bis[3-methyl-1-phenyl-4-[1-(3'-carboxyacryloyl)-2,2',6,6'-tetramethylpiperidyl-4]-aminomethylene-5-pyrazolonate] (compound XXVI, FIG. 3b)

A 250 ml erlenmeyer flask with a magnetic stirrer was filled with 14.86 g of Zinc complex (XVII) (Example 6), and 100 ml of benzene, which were dried over $CaH_2$. The flask contents were heated and stirred until all the complex was dissolved. The solution was cooled to room temperature and then 4 g of maleic anydride was added. The resulting mass was stirred at room temperature for about 12 hours. Then the precipitate was collected by filtration, washed with 50 ml of petroleum ether and dried. The compound was obtained with a yield of 17.88 (94.6%), and a m.p. of 203°–206° C. After crystallization from ethanol, the m.p. was 210°–212° C. λmax (ethanol): 295 and 255 nm. Found %: C 60.94; H 6.02; N 12.06. Gross formula: $C_{48}H_{58}N_8O_8Zn$. Calc. %: C 61.32; H 6.18; N 11.93.

(B) Compounds XXVII–XXXV (FIG. 3b)

Complexes XXVII–XXXV were obtained using the same procedure as in (A), with the following yield, gross formula, molecular mass, m.p., point of decomp., and λmax:

Zinc bis{3-methyl-1-phenyl-4-[1-(2-carboxymethylacryloyl)-2,2',6,6'-tetramethylpiperidyl-4]aminomethylene-5-pyrazolonate} (XXVII): 89%, $C_{50}H_{62}N_8O_8Zn$, 967, 199°–201° C., >240° C., λmax 295, 255 nm;

Zinc bis{3-methyl-1-phenyl-4-[1-(o-carboxybenzoyl)-2,2',6,6'-tetramethylpiperidyl-4]aminomethylene-5-pyrazolonate} (XXVIII): 85.5%, $C_{56}H_{62}N_8O_8Zn$, 1039, 267°–270° C., >280° C., λmax 295, 255, 230 nm;

Nickel bis{3-methyl-1-phenyl-4-[1-(o-carboxybenzoyl)-2,2',6,6'-tetramethylpiperidyl-4]aminomethylene-5-pyrazolonate} dihydrate (XXIX): 88.4%, $C_{56}H_{62}N_8O_8Ni\cdot 2H_2O$, 1068–1067, 243°–245° C., >260° C., λmax 300, 260 nm.

Zinc bis{3-methyl-1-phenyl-4-[1-(3-methyl-1-phenyl-5-pyrazolonylmethylidene-4)-2,2',6,6'-tetramethylpiperidyl-4]aminomethylene-5-pyrazolonate} (XXX): 92%, $C_{62}H_{70}N_{12}O_4Zn$, IIII, 194°–195° C., >250° C., λmax (ethanol) 310, 280, 220 nm.

Zinc bis{3-methyl-1-phenyl-4-[1-(3-methyl-1-phenyl-5-thiopyrazolonylmethylidene-4)-2,2',6,6'-tetramethylpiperidyl-4]aminomethylene-5-pyrazolonate} (XXXI): 85%, $C_{62}H_{70}N_{12}O_2S_2Zn$, 1147, 153°–155° C., >270° C., λmax (ethanol) 305, 270, 225 nm.

Cobalt bis{3-methyl-1-4-[1-(3-methyl-1-phenyl-5-pyrazolonylmethylidene-4)-2,2',6,6'-tetramethylpiperidyl-4] aminomethylene-5-pyrazolonate} dihydrate (XXXII): 89%, $C_{62}H70N_{12}O_4Co \cdot 2H_2O$, 1141, 186°–188° C., 240° C., λmax 300, 280, 220 nm.

Copper bis{3-methyl-1-phenyl-4-[1-(3-methyl-1-phenyl-5-pyrazolonylmethylidene-4)-2,2',6,6'-tetramethylpiperidyl-4]aminomethylene-5pyrazolonate} (XXXIII): 91%, $C_{62}H_{70}N_{12}O_4Cu$, 1109, 186°–189° C., >250° C., λmax (ethanol) 300, 280, 225 nm.

Zinc bis{3-methyl-1-phenyl-4-[1-(3-methyl-1-phenyl-5-thiopyrazolonylmethylidene-4)-2,2',6,6'-tetramethylpiperidyl-4]aminomethylene-5thiopyrazolonate] (XXXIV): 90,5%, $C_{62}H_{70}N_{12}S_4Zn$, 1175, 241°–243° C. (toluene), 270° C., λmax 330, 300, 260, 225 nm.

Nickel bis{3-methyl-1-phenyl-5-thiopyrazolonylmethylidene-4)-2,2',6,6'-tetramethylpiperidyl-4]aminomethylene-5-thiopyrazolonate} dihydrate (XXXV): 82%, $C_{62}H_{70}N_{12}S_4Ni \cdot 2H_2O$, 1203–1207, 191°–194° C., >240° C., λmax (ethanol) 300, 275, 260 nm.

EXAMPLE 8

Compounds XXXVI–XLII, FIG. 3b (A) Cooper bis{3-methyl-phenyl-4-carboxyaldphenylimine-5-[1-(3-methyl-1-phenyl-5-pyrazolonylmethylidene-4)-2,2',6,6'-tetramethylpiperidyl-4-aminopyrazolonate} (compound XXXVI, FIG. 3b)

A 250 ml erlenmeyer flask with a magnetic stirrer was filled with 10.48 g of 3-methyl-1-phenyl-5-[1-( 3-methyl-1-phenyl-5-pyrazolonylmethylidene-4)-2,2',6,6'-tetramethylpiperidyl-4]aminopyrazole-4-carboxyaldehyde (compound XII), 100 ml of ethanol, and 2 g of aniline. The flask contents were heated to 60° C. and stirred until the entire product was dissolved. To this solution, a solution of 2 g of copperacetate monohydrate in 30 ml of water was added. The resulting reaction mixture was stirred at 60° C. for 30 min and then was cooled to 15°–20° C., and the precipitate was collected by filtration. The precipitate was washed on the filter with 50 ml of cold water and dried at 60°–70° C.

The compound was obtained with a yield of 11.6 g (91%). The m.p. was 193°–196° C. After crystallization from dioxane the m.p. was 198°–200° C. λmax: 330, 280, and 240 nm. Found %: C 69.96, H 6.40, N 15.74. Gross formula: $C_{74}H_{82}N_{14}O_2Cu$. Calc. %: C 70.42, H 6.53, N 15.54.

(B) Compounds XXXVII–XLII (FIG. 3b)

Complexes XXXVII–XLII were obtained using the same procedure as in (A), with the following yield, gross formula, m.p., point of decomp., and λmax:

Zinc bis{3-methyl-1-phenyl-4-carboxyald(n-phenoxy)phenylimine-5-[1-(3-methyl-1-phenyl-5-thiopyrazolonylmethylidene-4)-2,2',6,6'-tetramethylpiperidyl-4]aminopyrorazolonate} (XXXVII): 85%, $C_{86}H_{90}N_{14}O_4Zn$, 260°–262° C. (dioxane), >290° C., λmax 335, 300, 280, 225 nm.

Zinc bis{3-methyl-1-phenyl-4-carboxyaldphenylimine-5-[1-(3-methyl-1-1phenyl-5-thiopyrazolonyl-methylidene-4)-2,2',6,6'-tetramethylpiperidyl-4]aminopyrorazolonate} (XXXVIII): 76%, $C_{74}H_{82}N_{14}S_2Zn$, 225°–227° C. (dioxane), >290° C., λmax 330, 300, 280, 225 nm.

Copper bis {3-methyl-1-phenyl-4-carboxyald(n-phenoxy)phenylimine-5-[1-(3-methyl-1-phenyl-5-thiopyrazolonylmethylidene-4)-2,2',6,6'-tetramethylpiperidyl-4]aminopyrazolonate} (XXXIX): 88%, $C_{86}H_{90}N_{14}O_2S_2Cu$, 254°–255° C. (dioxane), >290° C., λmax (EtOH) 340, 300, 270, 235 nm.

Copper bis{3-methyl-1-phenyl-4-carboxyald (n-butylcarboxy)-phenylimine-5-[1-(3-methyl-1-phenyl-5-pyrazolonylmethylidene-4)-2,2',6,6'-tetramethylpiperidyl-4]aminopyrazolonate} (XL):87,3%, $C_{84}H_{94}N_{14}O_6Cu$, 256°–258° C. (dioxane), >280° C., λmax (EtOH) 350, 305, 270, 235 nm.

Copper bis{3-methyl-1-phenyl-4-carboxyald(n-phenylamino)phenylimine-5-[1-(3-methyl-1-phenyl-5-pyrazolonylmethylidene-4)-2,2',6,6'-tetramethylpiperidyl-4]aminopyrazolonate} (XLI): 85%, $C_{86}H_{92}N_{16}O_2Cu$, 270°–273° C. (dioxane), >290° C., λmax 370, 320, 280, 245 nm.

Copper bis{3-methyl-1-phenyl-carboxyald(N-hydroxy-m,m'-ditretbutyl)phenylimine-5-[1-(3-methyl-1-phenyl-5-pyrazolonylmethylidene-4)-2,2',6,6'-tetramethylpiperidyl-4]-aminopyrazolonate} (XLII): 90%, $C_{90}H_{14}N_{14}O_4Cu$, 238°–240° C. (dioxane), >270° C., λmax (EtOH) 350, 330, 280, 235 nm.

EXAMPLE 9

(A) The light-stabilizing effect of Tinuvin P, complex II as in S.U. Pat. No. 956504, and compounds XVII and XX, on polystyrene films:

$M_0$— the molecular mass of poystyrene, estimated by viscosimetry method. M—the molecular mass of polystyrene (film thickness 0.04–0.045 mm) after irradiation by Hg Lamp (400 W) at 50° C., for 0, 20, 40, and 60 hours.

| Mol. mass of polystyrene/hours | Tinuvin P (1%) | Complex II (0.5%)(*) | XVII (0.25%) | XX (0.25%) |
|---|---|---|---|---|
| $M/M_0$ | 100 | 100 | 100 | 100 |
| $M_{20}/M_0$ | 79.3 | 87.3 | 89.8 | 92.5 |
| $M_{40}/M_0$ | 55.6 | 78.0 | 80.2 | 82.5 |
| $M_{60}/M_0$ | 38.5 | 74.0 | 78.0 | 80.3 |

(*)Complex II as in S.U. Pat. No. 956504: Nickel bis[3-methyl-1- phenyl-4-phenylamino-methylene-5-thiopyrazolonate].

(B) The light-stabilizing effect of Tinuvin 320 and compounds I, III, XVII, and XVIII on polycarbonate films

The absorption results obtained before (d) and after (d') irradiation of polycarbonate films (thickness 0.04–0.05 nm) by a Hg Lamp (400 W) at 50° C., for 3 hours:

|  | Tin 320 | I | III | XVII | XVIII |
|---|---|---|---|---|---|
| λmax (d) | 340 (1.55) | 295 (2.0) | 260 (1.8) | 295 (2.0) | 275 (1.4) |
|  | 300 (1.46) | 255 (1.35) |  | 255 (1.78) |  |
| λ'max (d') | 340 (1.5) | 295 (1.85) | 260 (1.75) | 295 (1.92) | 275 (1.35) |
|  | 300 (1.40) | 255 (1.28) |  | 255 (1.70) |  |

While the invention has been described with respect to a limited number of embodiments, it will be appreciated that many variations, modifications and other applications of the invention may be made.

What is claimed is:

1. Substituted pyrazoles of the formula I, where $R_1$ and $R_2$ are identical or different and each denotes hydrogen or alkyl or aryl, X is oxygen or sulphur, and

$R_3$ is hydrogen, alkyl, a derivative of carboxyacryloyl or carboxybenzoyl, or a derivative of pyrazole.

2. Compounds of the formula I as in claim 1, where $R_1$ is phenyl, $R_2$ is methyl,

X is oxygen or sulphur, and $R_3$ is H, $CH_3$, COCH=CHCOOH, $COC_6H_4COOH(o-)$, 3-Me-1-Ph-5-pyrazolonylmethylidene-4, or 3-Me-1-Ph-5-thiopyrazolonylmethylidene-4.

3. Substituted pyrazoles of the formula II, where $R_1$ and $R_2$ are identical or different and each denotes hydrogen or alkyl or aryl, Z is oxygen or N-aryl, and

$R_3$ is hydrogen, alkyl, a derivative of carboxyacryloyl or carboxybenzoyl, or a derivative of pyrazole.

4. Compounds of the formula II as in claim 3, where $R_1$ is phenyl, $R_2$ is methyl,

Z is O, $NC_6H_5$, $NC_6H_4OC_6H_5$, $NC_6H_4COOC_4H_9$ (m- or p-), or $NC_6H_2[p\text{-}OH,m,m'\text{-}C(CH_3)_3]$, and $R_3$ is H, $CH_3$, COCH=CHCOOH, $COC_6H_4COOH(o-)$, 3-Me-1-Ph-5-pyrazolonylmethylidene-4, or 3-Me-1-Ph-5-thiopyrazolonylmethylidene-4.

5. Metal complexes of the formula III, where $R_1$, $R_2$, $R_3$ and $R_4$ are identical or different and each denotes hydrogen or alkyl or aryl, X is oxygen or sulphur, $R_5$ and $R_6$ are identical or different and selected from the group consisting of hydrogen, alkyl, a derivative of carboxyacryloyl or carboxybenzoyl, and a derivative of pyrazole, and Me is a metal ion selected from the group consisting of Ni(II), Zn(II), Cu(II) and Co(II).

6. Metal complexes of the formula III as in claim 5, where $R_1$ is phenyl,

$R_2$ is methyl, $R_3$ is phenyl, $R_4$ is methyl,

X is oxygen or sulphur, $R_5$ and $R_6$ are identical and selected from the group consisting of H, $CH_3$, COCH=CHCOOH, $COC_6H_4COOH(o-)$, 3-Me-1-Ph-5-pyrazolonylmethylidene-4, and 3-Me-1-Ph-5-thiopyrazolonylmethylidene-4, and Me is a metal ion selected from the group consisting of Ni(II), Zn(II), Cu(II) and Co(II).

7. Metal complexes of the formula IV, where $R_1$, $R_2$, $R_3$ and $R_4$ are identical or different and each denotes hydrogen or alkyl or aryl, Z is oxygen or N-aryl, and $R_5$ and $R_6$ are identical or different and selected from the group consisting of hydrogen, alkyl, a derivative of carboxyacryloyl or carboxybenzoyl, and a derivative of pyrazole, and Me is a metal ion selected from the group consisting of Ni(II), Zn(II), Cu(II) and Co(II).

8. Metal complexes of the formula IV as in claim 7, where $R_1$ is phenyl,

$R_2$ is methyl, $R_3$ is phenyl, $R_4$ is methyl,

Z is O, $NC_6H_5$, $NC_6H_4OC_6H_5$, $NC_6H_4COOC_4H_9$ (m- or p-), or $NC_6H_2[p\text{-}OH,m,m'\text{-}C(CH_3)_3]$, $R_5$ and $R_6$ are identical and selected from the group consisting of H, $CH_3$, COCH=CHCOOH, $COC_6H_4COOH$(o-), 3-Me-1-Ph-5-pyrazolonylmethylidene-4, and 3-Me-1-Ph-5-thiopyrazolonylmethylidene-4, and Me is a metal ion selected from the group consisting of Ni(II), Zn(II), Cu(II) and Co(II).

9. Light stabilizers containing a substituted pyrazole, of the formula I, where $R_1$ and $R_2$ are identical or different and each denotes hydrogen or alkyl or aryl, X is oxygen or sulphur, and $R_3$ is hydrogen, alkyl, a derivative of carboxyacryloyl or carboxybenzoyl, or a derivative of pyrazole.

10. Light stabilizers containing a substituted pyrazole, of the formula II, where $R_1$ and $R_2$ are identical or different and each denotes hydrogen or alkyl or aryl, Z is oxygen or N-aryl, and $R_3$ is hydrogen, alkyl, a derivative of carboxyacryloyl or carboxybenzoyl, or a derivative of pyrazole.

11. Light stabilizers containing a substituted pyrazole, of the formula III, where

$R_1$, $R_2$, $R_3$ and $R_4$ are identical or different and each denotes hydrogen or alkyl or aryl, X is oxygen or sulphur, $R_5$ and $R_6$ are identical or different and selected from the group consisting of hydrogen, alkyl, a derivative of carboxyacryloyl or carboxybenzoyl, and a derivative of pyrazole, and Me is a metal ion selected from the group consisting of Ni(II), Zn(II), Cu(II) and Co(II).

12. Light stabilizers containing a substituted pyrazole, of the formula IV, where $R_1$, $R_2$, $R_3$ and $R_4$ are identical or different and each denotes hydrogen or alkyl or aryl, Z is oxygen or N-aryl, $R_5$ and $R_6$ are identical or different and selected from the group consisting of hydrogen, alkyl, a derivative of carboxyacryloyl or carboxybenzoyl, and a derivative of pyrazole, and Me is a metal ion selected from the group consisting of Ni(II), Zn(II), Cu(II) and Co(II).

13. A method for the synthesis of metal complexes as claimed in claim 5, which includes the reaction of:

(a) a compound as claimed in claim 1; and (b) metal acetate, wherein the metal ion is selected from the group consisting of Ni(II), Zn(II), Cu(II) and Co(II).

14. A method for the synthesis of metal complexes as claimed in claim 7, which includes the reaction of:

(a) a compound as claimed in claim 3; and (b) metal acetate, wherein the metal ion is selected from the group consisting of Ni(II), Zn(II), Cu(II) and Co(II).

15. A method for the synthesis of metal complexes as claimed in claim 5, wherein said $R_5$ and $R_6$ are selected from the group consisting of a derivative of carboxyacryloyl or carboxybenzoyl, and a derivative of pyrazole, which includes the reaction of:

(a) a metal complex as claimed in claim 5, wherein said $R_5$ and $R_6$ are selected from the group consisting of hydrogen and alkyl; and (b) anhydride or derivative of pyrazole.

16. A method for the synthesis of metal complexes as claimed in claim 7, wherein said $R_5$ and $R_6$ are selected from the group consisting of a derivative of carboxyacryloyl or carboxybenzoyl, and a derivative of pyrazole, which includes the reaction of:

(a) a metal complex as claimed in claim 7, wherein said $R_5$ and $R_6$ are selected from the group consisting of hydrogen and alkyl; and (b) anhydride or derivative of pyrazole.

17. A method for the synthesis of metal complexes as claimed in claim 6, which includes the reaction of:

(a) a compound as claimed in claim 2; and

(b) metal acetate of the formula $Me(OOCCH_3)_2$, wherein the metal ion is selected from the group consisting of Ni(II), Zn(II), Cu(II) and Co(II).

18. A method for the synthesis of metal complexes as claimed in claim 8, which includes the reaction of:

(a) a compound as claimed in claim 4; and (b) metal acetate of the formula $Me(OOCCH_3)_2$, wherein the metal ion is selected from the group consisting of Ni(II), Zn(II), Cu(II) and Co(II).

19. A method for the synthesis of metal complexes as claimed in claim 6, wherein said $R_5$ and $R_6$ are selected from the group consisting of COCH=CHCOOH, $COC_6H_4COOH(o\text{-})$, 3-Me-1-Ph-5-pyrazolonylmethylidene-4, and 3-Me-1-Ph-5-thiopyrazolonylmethylidene-4, which includes the reaction of:

(a) a metal complex as claimed in claim 6, wherein said $R_5$ and $R_6$ are selected from the group consisting of H and $CH_3$; and (b) components selected from the group consisting of maleic, itaconic or phthalic anhydride, 3-Me-1-Ph-5-hydroxypyrazole-4-carboxyaldehyde, and 3-Me-1-Ph-5-mercaptopyrazole-4-carboxyaldehyde.

20. A method for the synthesis of metal complexes as claimed in claim 8, wherein said $R_5$ and $R_6$ are selected from the group consisting of COCH=CHCOOH, $COC_6H_4COOH(o\text{-})$, 3-Me-1-Ph-5-pyrazolonylmethylidene-4, and 3-Me-1-Ph-5-thiopyrazolonylmethylidene-4, which includes the reaction of:

(a) a metal complex as claimed in claim 8, wherein said $R_5$ and $R_6$ are selected from the group consisting of H and $CH_3$; and (b) components selected from the group consisting of maleic, itaconic or phthalic anhydride, 3-Me-1-Ph-5-hydroxypyrazole-4-carboxyaldehyde, and 3-Me-1-Ph-5-mercaptopyrazole-4-carboxyaldehyde.

* * * * *